(12) United States Patent
Chen et al.

(10) Patent No.: US 6,800,499 B2
(45) Date of Patent: Oct. 5, 2004

(54) PROCESS FOR PREPARING A HYDROGEN SENSOR

(75) Inventors: Huey-Ing Chen, Tainan (TW);
Wen-Chau Liu, Tainan (TW); Yen-I Chou, Tainan (TW); Chin-Yi Chu, Tainan (TW); Hsi-Jen Pan, Tainan (TW)

(73) Assignee: National Science Council, Taipei (TW)

( * ) Notice: Subject to any disclaimer, the term of this patent is extended or adjusted under 35 U.S.C. 154(b) by 0 days.

(21) Appl. No.: 10/157,251

(22) Filed: May 28, 2002

(65) Prior Publication Data

US 2002/0182767 A1 Dec. 5, 2002

Related U.S. Application Data

(63) Continuation of application No. 09/729,883, filed on Dec. 5, 2000, now abandoned, which is a continuation-in-part of application No. 09/564,742, filed on May 4, 2000, now Pat. No. 6,293,137, which is a continuation-in-part of application No. 09/321,535, filed on May 28, 1999, now Pat. No. 6,160,278.

(51) Int. Cl.[7] .............................................. H01L 21/00
(52) U.S. Cl. ............................ 438/22; 438/48; 438/49; 438/93; 438/597
(58) Field of Search ............................ 438/22, 48, 49, 438/93, 597, 678; 257/252, 253, 472, 486

(56) References Cited

U.S. PATENT DOCUMENTS

| | | | | |
|---|---|---|---|---|
| 4,795,717 A | * | 1/1989 | Okamura ..................... | 438/171 |
| 4,804,410 A | * | 2/1989 | Haga et al. ................. | 106/115 |
| 5,285,084 A | * | 2/1994 | von Windheim et al. ..... | 257/77 |
| 5,517,054 A | * | 5/1996 | Huang et al. ................ | 257/472 |
| 6,160,278 A | * | 12/2000 | Liu et al. ..................... | 257/252 |

OTHER PUBLICATIONS

Hasegawa et al., "Unified Disorder Induced Gap State Model for Insulator–semiconductor and Metal–semiconductor Interfaces", J. Vac. Sci. Techno. 4:1130–1138, 1986.

Lechuga et al., "A New Hydrogen Sensor Based on a Pt/GaAs Schottky Diode", J. Electrochem. Soc. 138:159–162, 1991.

Dutta et al., "Deposition and Characterization of Zinc Oxide Thin Films for Hydrogen Sensor Devices", Materials Science and Engineering 31–35, 1992.

Yadava et al., "A Titanium Dioxide–Based Mos Hydrogen Sensor", Solid State Electronics 33:1229–1234, 1990.

* cited by examiner

Primary Examiner—Hsien Ming Lee
(74) Attorney, Agent, or Firm—Fish & Richardson P.C.

(57) ABSTRACT

A high-sensitivity Pd/InP hydrogen sensor was made by a) forming an n-type or p-type semiconductor film on a semiconductor substrate; b) forming a patterned first metal electrode on the semiconductor film, wherein the first metal electrode forms an Ohmic contact with the semiconductor film; and c) forming a second metal electrode on the semiconductor film, the second metal electrode being isolated from the first metal electrode, wherein the second metal electrode forms a Schottky contact with the semiconductor film, wherein a thickness of the second metal electrode and a material of which the second metal electrode is made enable a Schottky barrier height of the Schottky contact to decrease when hydrogen contacts the second metal electrode. The second metal electrode can be physical vapor deposited or electroless plated.

36 Claims, 11 Drawing Sheets

PROCESS FOR PREPARING A HYDROGEN SENSOR

CROSS-REFERENCE TO RELATED APPLICATION

This present application is a continuation of U.S application Ser. No. 09/729,883, filed Dec. 5, 2000 now abandoned, which in turn is a continuation-in-part of U.S. application Ser. No. 09/564,742, filed May 4, 2000, now U.S. Pat. No. 6,293,137, and a continuation-in-part of U.S. application Ser. No. 09/321,535, filed May 28, 1999, now U.S. Pat. No. 6,160,278. The disclosures of the prior applications are considered part of, and are incorporated by reference in, the disclosure of this application.

FIELD OF THE INVENTION

The present invention is related to a fabrication process of a metal-semiconductor hydrogen sensor, and in particular, a fabrication process of a metal-semiconductor hydrogen sensor using an electroless plating method to form a metal electrode of the hydrogen sensor.

BACKGROUND OF THE INVENTION

Due to the technology developments, modern industrial and medical applications use a large quantity of hydrogen as a raw material or other purposes. Hydrogen, however, is a flammable and explosive gas. When the concentration of leakage hydrogen reaches 4.65 vol % or more in air, a hazard of explosion will take place. Therefore, on considerations of industrial safety and environmental concern, hydrogen sensors are widely used in factories, laboratories and hospitals for accurately monitoring the concentration of leakage hydrogen. The large volume and high production cost are disadvantages of conventional hydrogen sensors. Besides, most of the sensors are passive elements, so that other additional equipment or a conversion circuit is required to perform the analysis or amplification. Therefore, the conventional hydrogen sensors can not become intelligent sensors. As a result, the development of a new and effective hydrogen sensor that is intelligent and of the active type has become an important topic in modern industries.

In recent years, due to the advance of silicon semiconductor technology, much attention has been attracted on the use of a Pd metal-oxide-semiconductor (MOS) structure as a semiconductor hydrogen sensor. The reason for using the Pd metal in the hydrogen sensor lies in that Pd has a good catalytic activity and can dissociate the hydrogen molecule adsorbed to the surface into hydrogen atoms. A portion of the hydrogen atoms diffuses through the Pd metal and is adsorbed to the interface between the metal and the oxide layer. These hydrogen atoms, after polarization, cause a change in the Schottky barrier height between the oxide layer and the silicon semiconductor and thus the electrical properties of the device. In the early days, I. Lundstrom proposed a $Pd/SiO_2/Si$ MOS field effect transistor structure with a Pd gate [Lundstrom, M. S. Shivaraman, and C. Svensson, J. Appl. Phys., 46, 3876 (1975)]. After the hydrogen being adsorbed to the Pd gate, the altered threshold voltage and terminal capacitance are used as the two bases for the detection of hydrogen. However, the use of a three-terminal device to realize the functions of a two-terminal device not only increases the cost, but also has increases process difficulties. Furthermore, the quality of the oxide layer will also influence the hydrogen detection capability. The quality of an oxide layer becomes unstable when the growth of the thin oxide layer is contaminated by ions. This results in the surface state pinning of Fermi-level of silicon semiconductor. Therefore, Schottky barrier height is less influenced by the polarized hydrogen atoms and subsequently the hydrogen sensitivity is lower. Many researches were focused on how to improve such a problem. For example, A. Dutta et al. used zinc oxide (ZnO) [A. Dutta, T. K. Chaudhuri, and S. Basu, Materials Science Engineering, B14, 31 (1992)] and L. Yadava et al. used titanium dioxide ($TiO_2$) to replace the oxide layer of silicon dioxide [L. Yadava, R. Dwivedi, and S. K. Srivastava, Solid-St. Electron., 33, 1229 (1990)]. On the other hand, the use of a two-terminal type Schottky barrier diode seems to be a more intuitive approach. Without the unstable factors of the oxide layer, the sensitivity of the device to hydrogen has a significant improvement. Therefore, for example, M. C. Steelee et al. proposed a Pd/CdS structure [M. C. Steele and B. A. Maciver, Appl. Phys. Lett., 28, 687 (1976)], and K. Ito et al. proposed a Pd/ZnO structure [K. Ito, Surface Sci., 86, 345 (1982)]. The using II-VI compound semiconductor as the material is mainly due to the less effect of surface states of II-VI compound semiconductor as compared to the polarized hydrogen atoms.

Lechuga et al. (1991) prepared a hydrogen sensor of a Schottky barrier diode type on a substrate of II-V compound, wherein Pt metal was vacuum evaporated on a GaAs substrate [L. M. Lechuga, A. Calle, D. Golmayo, P. Tejedor and F. Briones, J Electrochem. Soc., 138, 159 (1991)]. They reported that a surface state pinning of Fermi-level of semiconductor occurred when the film was deposited by a high energy means, and thus the Schottky barrier height is less susceptible to be affected by polarized hydrogen atoms. These phenomena may be explained by the theory of DIGS model proposed by Hasegawa et al. [H. Hasegawa and H. Ohno, J. Vac. Sci. Technol., B5, 1130 (1986)].

In past years, wet method (also called solution method) was seldom adopted in a fabrication process of a semiconductor device, because its plating solution contains many chemical components and it involves complicated chemical reactions. However, the electroplating method gradually exhibits its advantages in the latter stages of the semiconductor fabrication process in view of its superior capabilities in planarization, step coverage, and the plugging required by fabricating the multi-level interconnects. In particular, electroless plating is easy to be carried out with lower cost and energy consumption, and is suitable to be adopted in a continuous process for industrial mass production.

SUMMARY OF THE INVENTION

A primary objective of the present invention is to provide a process for preparing a metal-semiconductor type hydrogen sensor.

Another objective of the present invention is to provide a process for preparing a metal-semiconductor type hydrogen sensor, wherein a metal electrode of the hydrogen sensor is formed by electroless plating technique.

The hydrogen sensor prepared according to the process of the present invention comprises:
  a semiconductor substrate;
  an n-type or p-type semiconductor film formed on said semiconductor substrate; and
  an anode and a cathode formed on the same surface of said semiconductor film and isolated from each other, wherein a first metal as said cathode forms an Ohmic contact with said semiconductor film and a second metal as said anode forms a Schottky contact with said semiconductor film, wherein a thickness of said second metal and a material of which said second metal is made enable a Schottky barrier height of said Schottky contact to decrease when hydrogen contacts an exposed surface of said second metal.

In the present invention, the material and the thickness of said second metal electrode enable the hydrogen molecule to dissociate into hydrogen atoms when the hydrogen gas comes into contact with the exposed surface of said second metal electrode. Also, said hydrogen atoms diffuse through said second metal electrode, so said Schottky barrier height decreases.

A process for preparing a hydrogen sensor according to the present invention comprises the following steps:

a) forming an n-type or p-type semiconductor film on a semiconductor substrate;

b) forming a patterned first metal electrode on said semiconductor film, wherein said first metal electrode forms an Ohmic contact with said semiconductor film; and c) forming a second metal electrode on said semiconductor film, said second metal electrode being isolated from said first metal electrode, wherein said second metal electrode forms a Schottky contact with said semiconductor film, wherein a thickness of said second metal electrode and a material of which said second metal electrode enables a Schottky barrier height of said Schottky contact to decrease when hydrogen gas is contacted with said second metal electrode.

Preferably, the process of the present invention further comprises thermal annealing said first metal electrode to enhance electric characteristics of said Ohmic contact after the formation of said first metal electrode in step b). More preferably, said thermal annealing is carried out at a temperature ranging from 300° C. to 500° C. for a period from 20 seconds to 5.0 minutes.

Preferably, step b) of the process of the present invention comprises the following sub-steps:

I. coating a photoresist layer on said semiconductor film;

II. imagewise exposing said photoresist layer with a photomask;

III. developing said imagewise exposed photoresist layer to transfer a pattern of said photomask to said photoresist layer, so that a patterned photoresist layer is formed, and thus said semiconductor film is partially exposed;

IV. depositing a first metal on the partially exposed semiconductor film; and

V. lifting-off said patterned photoresist layer to form said patterned first metal electrode on said semiconductor film.

Preferably, step c) of the process of the present invention comprises the following sub-steps:

i. coating a photoresist layer on a whole surface of said semiconductor film containing said first metal electrode;

ii. imagewise exposing said photoresist layer with a photomask;

iii. developing said imagewise exposed photoresist layer to transfer a pattern of said photomask to said photoresist layer, so that a patterned photoresist layer is formed, and thus said semiconductor film is partially exposed;

iv. depositing a second metal on the partially exposed semiconductor film; and v. lifting-off said patterned photoresist layer to form said second metal electrode on said semiconductor film.

Preferably, said depositing in sub-step IV) of step b) and in sub-step iv) of step c) are carried out by physical vapor deposition such as vacuum evaporation.

Preferably, said second metal electrode is Pd, Pd alloy or Pt, and more preferably Pd. Said second metal electrode, preferably, has a thickness of 0.30 to 5 micron.

Preferably, said depositing in sub-step iv) of step c) is carried out by electroless plating technique. Said electroless plating, preferably, comprises contacting said partially exposed semiconductor film with a plating solution for a period of time, wherein said plating solution is an aqueous solution comprising metal ions of said second metal electrode, such as palladium ions, a complexing agent, a reducing agent, a pH buffer and a stabilizer. Said palladium ions are preferably provided by dissolving a palladium salt or palladium halide into water. Said complexing agent preferably is selected from the group consisting of ethylenediamine, tetramethylethylenediamine, ethylenediaminetetraacetic acid (EDTA) and N,N,N',N'-tetrakis(2-hydroxypropyl)-ethylenediamine. Said reducing agent is preferably selected from the group consisting of hydrazine, hypophosphite, borohydride and formaldehyde. Said pH buffer is preferably boric acid or ammonia solution. Said electroless plating, preferably, comprises contacting said partially exposed semiconductor film with said plating solution having a pH value of 9–12 and a temperature of 20–70° C. for a period of time ranging from 1 minute to 1 hour.

Preferably said electroless plating, prior to contacting said partially exposed semiconductor film with said plating solution, further comprises undergoing a sensitization treatment by contacting said partially exposed semiconductor film with a sensitizing solution, which is an acidic solution containing stannous ions, for a period of time, for example from 5 to 10 minutes; and subsequently undergoing an activation treatment by contacting said partially exposed semiconductor film with an activating solution, which is an acidic solution containing palladium ions, for a period of time, for example from 5 to 10 minutes.

Preferably, said semiconductor substrate is made of a semi-insulating InP or GaAs material.

Preferably, said semiconductor film formed in step a) of the process of the present invention is an n-type III-V compound, and more preferably, said n-type III-V compound has a doping concentration of $5 \times 10^{15}$ to $1 \times 10^{18}$ cm$^{-1}$. An appropriate thickness of said n-type III-V compound is 0.050 micron to 10 micron. Said n-type III-V compound can be n-type InP (n-InP) or n-type GaAs, and preferably is n-InP.

Preferably, said semiconductor film is formed by a metal organic chemical vapor deposition or molecular beam epitaxy deposition in step a) of the process of the present invention.

Preferably, said first metal electrode of the hydrogen sensor of the present invention is an AuGe alloy or AuGeNi alloy, and more preferably an AuGe alloy. Said AuGe alloy preferably has a thickness of 0.30 micron to 5 micron.

Preferably, said second metal electrode of the hydrogen sensor of the present invention has a C shape or a C-like shape, and said first metal electrode has a shape corresponding to the shape of said second metal electrode such that said first metal electrode is encompassed by said second metal electrode. Alternatively, said first metal electrode has a C shape or a C-like shape and said second metal electrode has a shape corresponding to the shape of said first metal electrode such that said second metal electrode is encompassed by said first metal electrode.

In order to further elaborate the objectives, characteristics and merits of the-present invention, preferred embodiments together with related figures are disclosed hereinafter.

DETAILED DESCRIPTION OF PREFERRED EMBODIMENTS OF THE INVENTION

Figure 1:
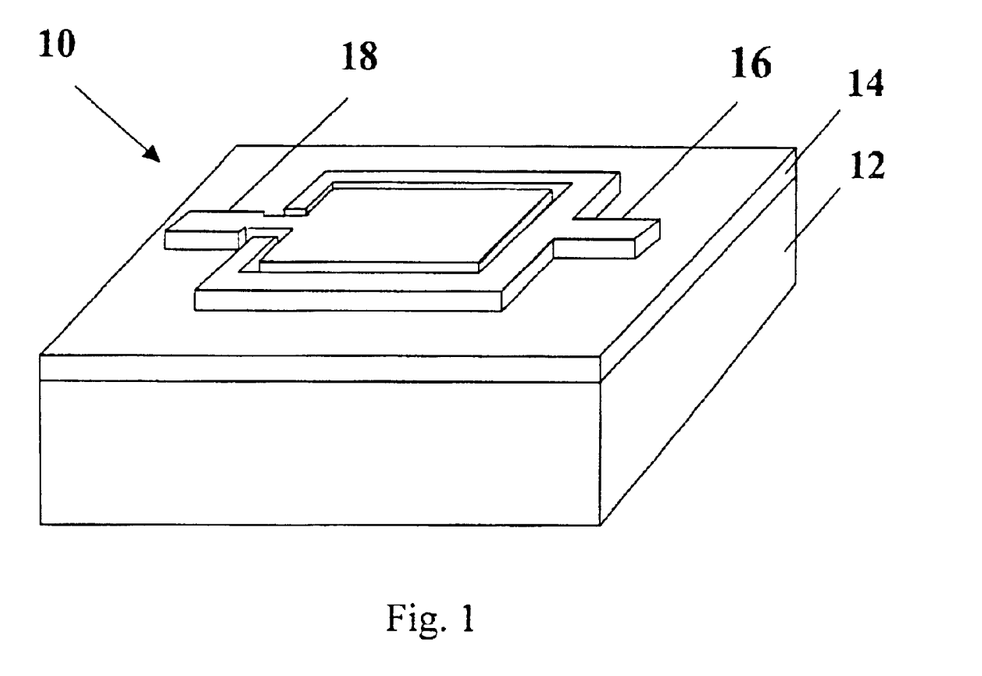
FIG. 1 is an illustrative perspective view of a Pd/InP hydrogen sensor made according to a first preferred embodiment of the present invention.

Referring to FIG. 1, a highly sensitive Pd/InP hydrogen sensor 10 made according to a first preferred embodiment of the present invention comprises: a semi-insulating InP substrate 12; an n-type InP (n-InP) film 14 on said semi-insulating InP substrate 12; an Ohmic contact metal layer of AuGe alloy 16 and a Schottky contact metal layer of Pd metal 18 both on said n-InP film 14, wherein said Ohmic contact metal layer 16 and said Schottky contact metal layer 18 are adjacent to and isolated from each other.

In said high-sensitivity Pd/InP hydrogen sensor 10, said n-InP film 14 is a high quality n-InP film grown on said semi-insulating InP substrate 12 by a metal organic chemical vapor deposition (MOCVD) process or molecular beam epitaxy (MBE) process. The number of the surface states is greatly reduced by this technique. The Schottky barrier height between metal-semiconductor is therefore closely related to the number of the polarized hydrogen atoms. Furthermore, the InP material has a high hydrogen coverage. This means a very low hydrogen content in air can significantly be detected to alter the Schottky barrier height. Such a property is applicable on a low concentration detection of less than 1%. In terms of the temperature characteristics, the bandgap of the InP material is about 1.35 eV which is larger than silicon; therefore, the InP material has a rather good performances for various temperatures. Most importantly, the growth of the InP material and the fabrication process thereof are mature, and have been widely used in the industry of optoelectronic or microwave integrated circuits. The hydrogen sensor of the present invention can thus be integrated with an optoelectronic device into a multi-functional intelligent sensor capable of detecting optoelectronic properties and hydrogen simultaneously. It is believed that the hydrogen sensor of the present invention has a great potential in various applications.

The Ohmic contact metal layer 16 and the Schottky contact metal layer 18 of the hydrogen sensor can be formed by any conventional deposition methods, such as the vacuum evaporation used in the first preferred embodiment of the present invention; however, in a second preferred embodiment of the present invention a low temperature and energy saving semiconductor fabrication method, electroless plating, was used to grow the Schottky contact metal layer 18 on said n-InP film 14.

For the electroless plating technique, an autocatalytic oxidation-reduction reaction is taking place in the plating solution, which may be expressed as follows in the second preferred embodiment of the present invention:

$$2Pd^{2+}{}_{(aq)} + N_2H_{4(aq)} + 4OH^-{}_{(aq)} \rightarrow 2Pd_{(s)} + N_{2(g)} + 4H_2O_{(l)}$$

In addition to the $Pd^{2+}$ precursor, for example a palladium salt such as $PdCl_2$, and the reducing agent, hydrazine ($N_2H_4$), the plating solution may further contains other additives in practical use as follows:

a. A complexing agent for $Pd^{2+}$ ions, which serves to prevent chemical reduction of the $Pd^{2+}$ ions in solution phase while permitting selective reduction on the surface of the substrate. The complexing agent can control the concentration of $Pd^{2+}$ ions in the plating solution. The complexing agent used in the present invention can affect the rate of electroless plating and the microstructure of the plated metal layer. As a result, it can affect the characteristics of the Schottky contact of the hydrogen sensor and the detection performance thereof.

b. A promoter for accelerating the electroless plating rate and enhancing the ductility of the plated metal film. A small amount of an organic compound as the promoter is added to increase the plating rate to meet the industrial mass production need.

c. A stabilizer for reducing the auto-decomposition of the electroless plating system. In general, the stabilizer has no catalytic activity and will even reduce the reaction rate, therefore only a trace amount thereof is added.

d. A pH buffer for keeping the pH value of the plating solution, and in turns for avoiding the change of the electroless plating rate. During the reaction of electroless plating, OH⁻ ions are consumed as shown in the equation above, and thus the pH value of the plating solution will change. Therefore, the pH buffer is used to keep the pH value constant.

EXAMPLE 1

Vacuum Evaporation

A high-sensitivity Pd/InP hydrogen sensor 10 as shown in FIG. 1 was prepared. The fabrication process includes: preparing a semi-insulating InP substrate 12; growing a high quality n-type InP film 14 on said semi-insulating InP substrate 12 by an metal organic chemical vapor deposition (MOCVD) process, the concentration and the thickness of said n-type InP film 14 being $1 \times 10^{17}$ cm$^{-3}$ and 3000 Å, respectively; and separately evaporating an AuGe Ohmic contact metal layer 16 as a cathode and a Pd metal Schottky contact metal layer 18 as an anode on the surface of said n-type InP film 14 by the conventional photolithography and vacuum evaporation techniques. A thermal annealing at 400° C. was carried out for about one minute following the deposition of the AuGe Ohmic contact metal layer 16.

Figure 2A:
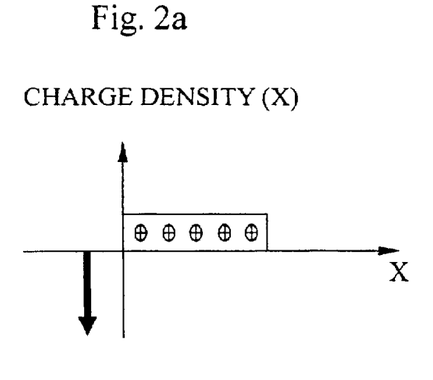
FIGS. 2a and 2a' are the charge density distribution and energy band diagrams of the hydrogen sensor shown in FIG. 1, respectively, wherein hydrogen is not detected.
Figure 2B:
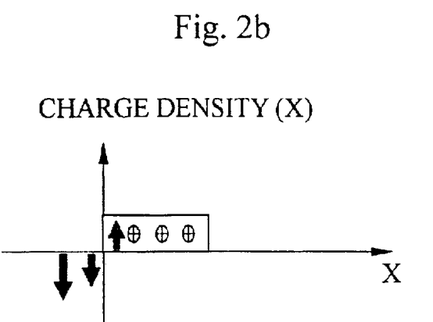
FIGS. 2b and 2b' are the charge density distribution and energy band diagrams of the hydrogen sensor shown in FIG. 1, respectively, wherein hydrogen is detected.

The charge density distribution and energy band diagrams of the resulting hydrogen sensor are shown in FIGS. 2a and 2a' where hydrogen is not detected; and FIGS. 2b and 2b' where hydrogen is detected. Prior to introducing hydrogen gas, the charge distribution of the said sensor at the interface of the Pd metal 18 and the n-type InP film 14 is at equilibrium. A metal-semiconductor Schottky barrier height ($\phi_B$) is thus formed as shown in FIGS. 2a and 2a'. After hydrogen gas has been introduced, due to the catalytic property of Pd metal 18, the hydrogen molecules will dissociate into hydrogen atoms when the hydrogen molecules are adsorbed on the surface of the Pd metal 18. Most of the dissociated hydrogen atoms will diffuse through the Pd metal 18 and create an excess of charged state resulting in a dipole layer at the interface between the Pd metal 18 and the n-type InP film 14. Such a dipole layer will cause the original equilibrium state of charge distribution shifting to a new one. Consequently, the width of the depletion region of the n-type InP semiconductor is reduced and thereby the Schottky barrier height ($\phi_B$), is decreased as shown in FIGS. 2b and 2b'.

Figure 3:
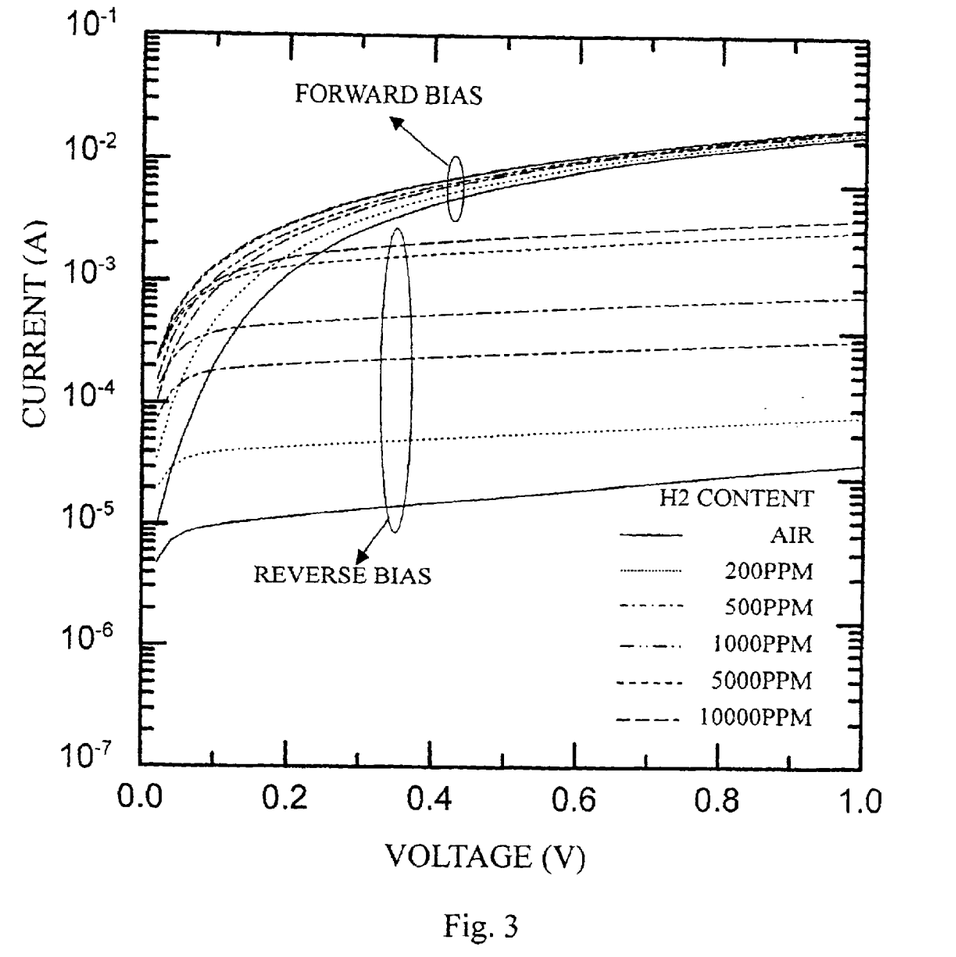
FIG. 3 shows the current-voltage characteristics of the hydrogen sensor shown in FIG. 1, when it was used to measure air and atmospheres which contain 200 ppm, 500 ppm, 1000 ppm, 5000 ppm and 10000 ppm of hydrogen, respectively.

FIG. 3 shows the current-voltage characteristics of the hydrogen sensor prepared in this example, when it was used to measure air and atmospheres which contain 200 ppm, 500 ppm, 1000 ppm, 5000 ppm and 10000 ppm of hydrogen, respectively. In this figure, a forward bias is defined as a positive voltage being applied to the said Schottky contact relative to the said Ohmic contact. On the contrary, a reverse bias is for a negative voltage. Due to the decrease of Schottky barrier height as the hydrogen content increases, correspondingly the current becomes larger. As it can be seen from FIG. 3, either a forward bias current or a reverse bias current increases as the hydrogen content increases. Moreover, it is obvious that the increase of a reverse current is proportional to the hydrogen content.

Figure 4:
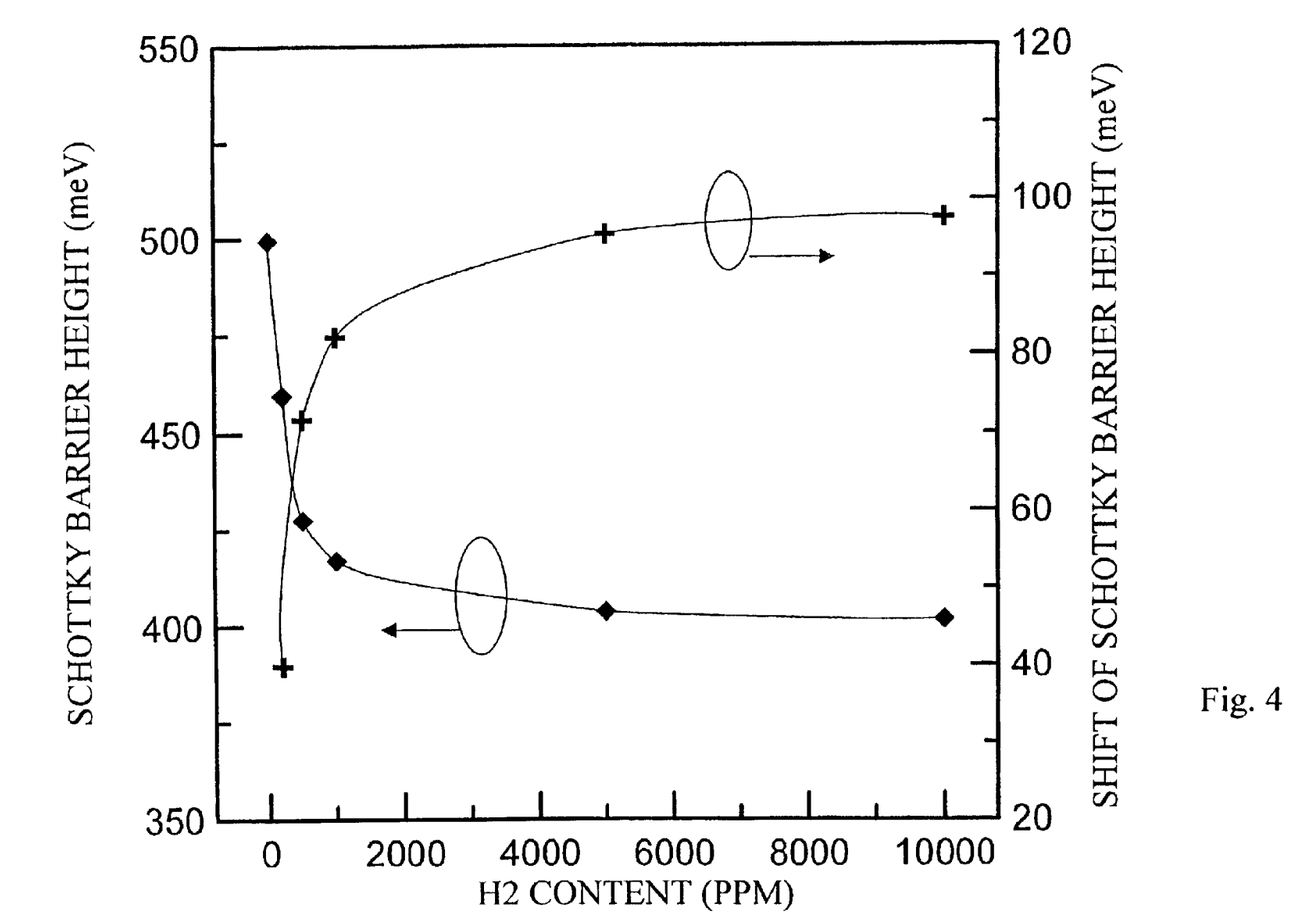
FIG. 4 shows the Schottky barrier height as a function of hydrogen content for the hydrogen sensor shown in FIG. 1.

FIG. 4 shows the Schottky barrier height as a function of hydrogen content for the hydrogen sensor prepared in this example. The barrier height in air is about 500 meV and it creases along with an increase of the hydrogen content. When the hydrogen content is larger than 0.5%, the barrier height reaches a minimum and the forward current conduction is very close to the Ohmic contact.

Figure 5:
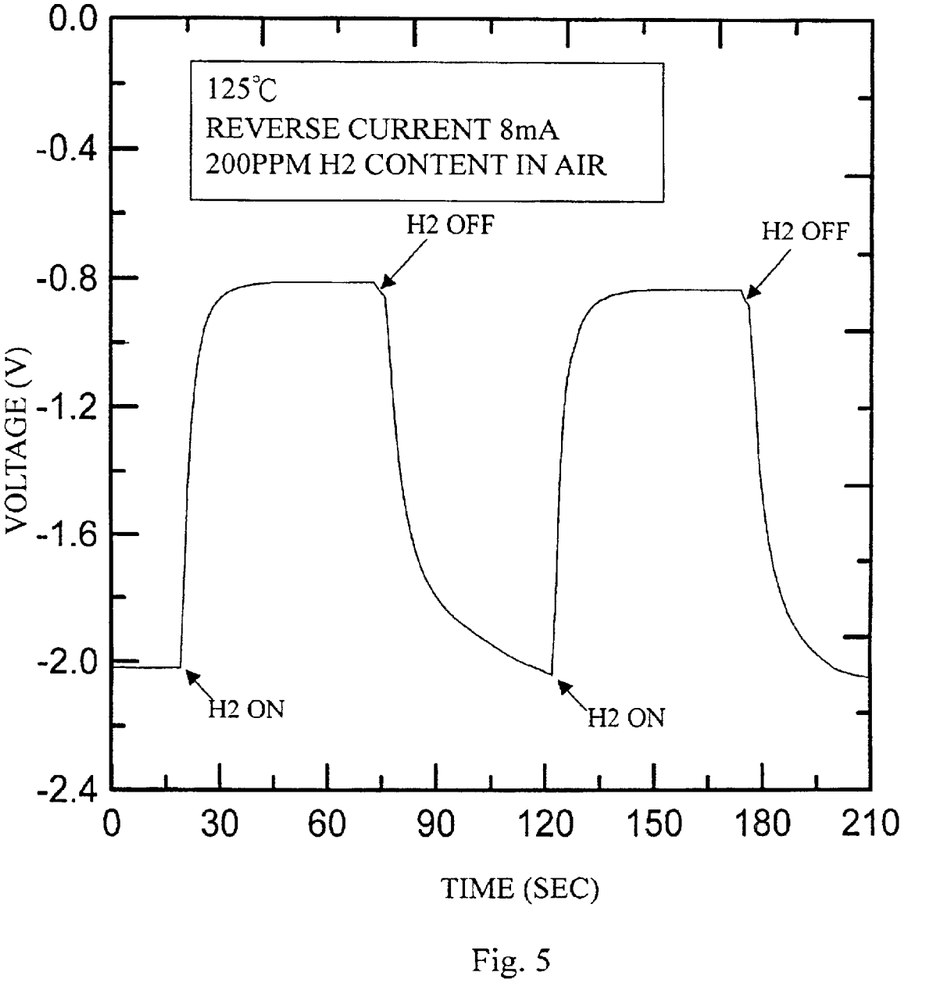
FIG. 5 shows transient responses measured at 125° C. for the hydrogen sensor shown in FIG. 1. An air flow containing 200 ppm of hydrogen was introduced into a test chamber at 500 ml/min. The reverse current of 8 mA was maintained between the two electrodes of the Schottky contact metal layer 18 and the Ohmic contact metal layer 16.

FIG. 5 shows transient responses measured at 125° C. for the hydrogen sensor prepared in this example. The air flow containing 200 ppm of hydrogen was introduced into the test chamber at a flow rate of 500 ml/min. The reverse current of 8 mA was maintained. Due to the dipole layer formed by the dissociated hydrogen atoms, the reverse current increases. Correspondingly, the voltage between the two electrodes decreases for about 1.2 V. On the other hand, when the hydrogen gas was turned off, the sensor was exposed to air. Therefore, the hydrogen atoms are desorbed from the surface of the Pd metal by recombining into hydrogen molecules or forming water molecules with oxygen. This results in recovering the voltage to the origin. We define the reaction time and recovery time as the times that are required to reach 90% reaction of their steady values, respectively. It can be seen from FIG. 5 that the reaction time of the sensor is about 5 seconds and the recovery time is about 12 seconds. Furthermore, a second cycle of the transient voltage response was obtained by repeating the first one. A comparison of the two cycles indicates a high reproducibility of the results.

Figure 6:
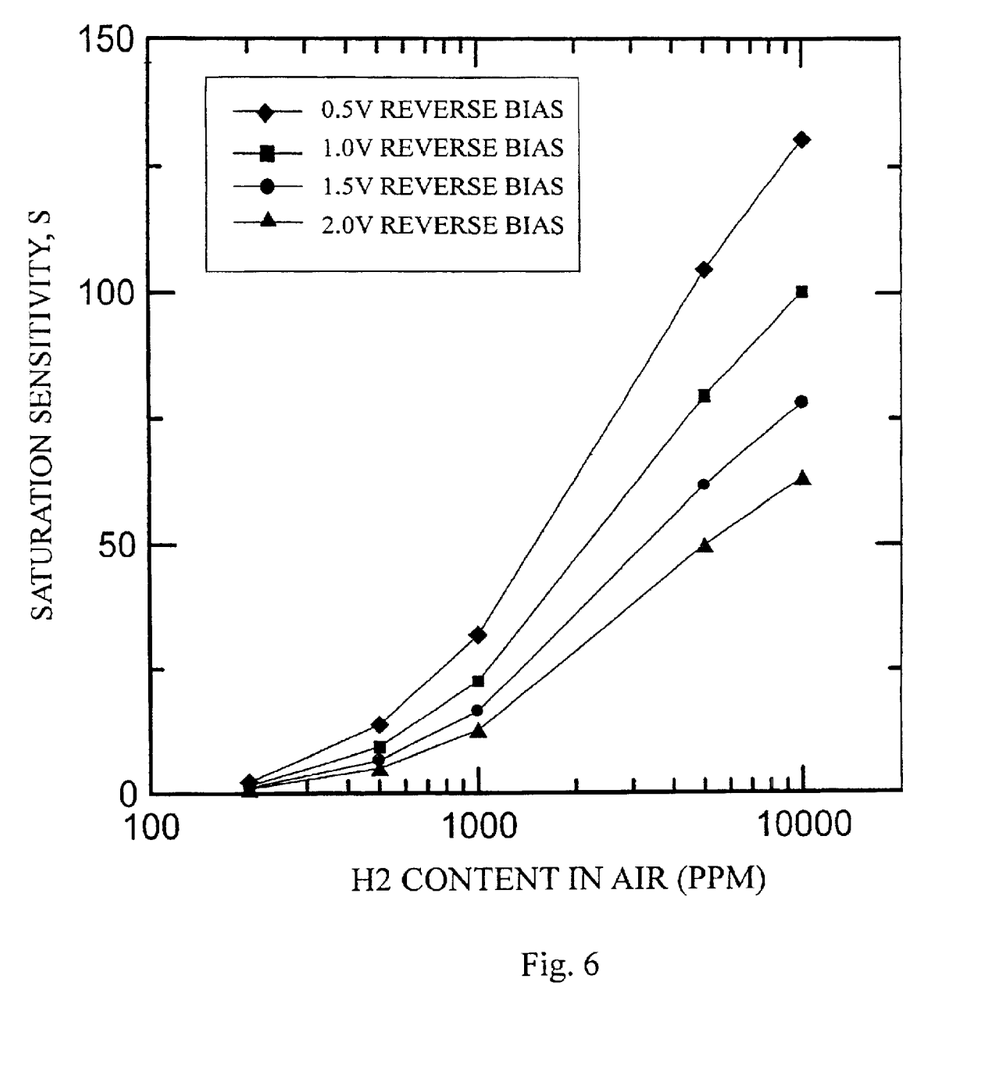
FIG. 6 shows the saturation sensitivity as a function of hydrogen content for the hydrogen sensor shown in FIG. 1 under various reverse voltages of 0.5 V (black diamond), 1.0 V (black square), 1.5 V (black round dot) and 2.0 V (black triangle), respectively.

FIG. 6 shows the saturation sensitivity as a function of hydrogen content for the hydrogen sensor prepared in this example. The saturation sensitivity, S, is defined as the ratio of the current variation under a constant reverse voltage to the reference current, $(I_{H_2}-I_{air})/I_{air}$. The results in FIG. 6 clearly show that the sensitivity increases monotonically along with the increase of the hydrogen content. At a reverse bias of 0.5 V, a saturation sensitivity of the hydrogen sensor can reach up to 130 in the air atmosphere containing 1% hydrogen. The saturation sensitivity can reach 2 even in the air atmosphere containing 200 ppm hydrogen.

EXAMPLE 2

Electroless Plating

A high-sensitivity Pd/InP hydrogen sensor 10 as shown in FIG. 1 was prepared by using the procedures similar to those used in Example 1, except that the Pd metal Schottky contact metal layer 18 was formed by electroless plating after the AuGe Ohmic contact metal layer 16 had been vacuum evaporated and thermally annealed. A photoresist layer was coated on the whole surface of the n-type InP film 14 having a doping concentration of $5 \times 10^{17}$ cm$^{-3}$ and the AuGe Ohmic contact metal layer 16, imagewise exposed with a photomask, and then developed to form a patterned photoresist layer, so that a portion of the n-type InP film 14 was exposed. The semiconductor substrate as a whole was immersed in an electroless plating bath at 30° C. for 10 minutes, so that a Pd metal layer was plated on the exposed portion of the n-type InP film 14. The semiconductor substrate was removed from the plating bath, washed with water, and then the patterned photoresist layer was lifted-off to obtain the Pd metal Schottky contact metal layer 18 formed on the n-type InP film 14. The plating bath was an aqueous solution having the following composition:

| | |
|---|---|
| PdCl$_2$ | 2.7 g/L |
| NH$_4$OH (28%) | 195 ml/L |
| Na$_2$EDTA | 35 g/L |
| N$_2$H$_4$ (1 M) | 100 ml/L |
| Thiourea | 0.0006 g/L |

The Pd metal Schottky contact metal layer 18 was examined with scanning electron microscopy, and found that it has a dense matrix with a thickness about 6000 Angstrom.

Figure 7:
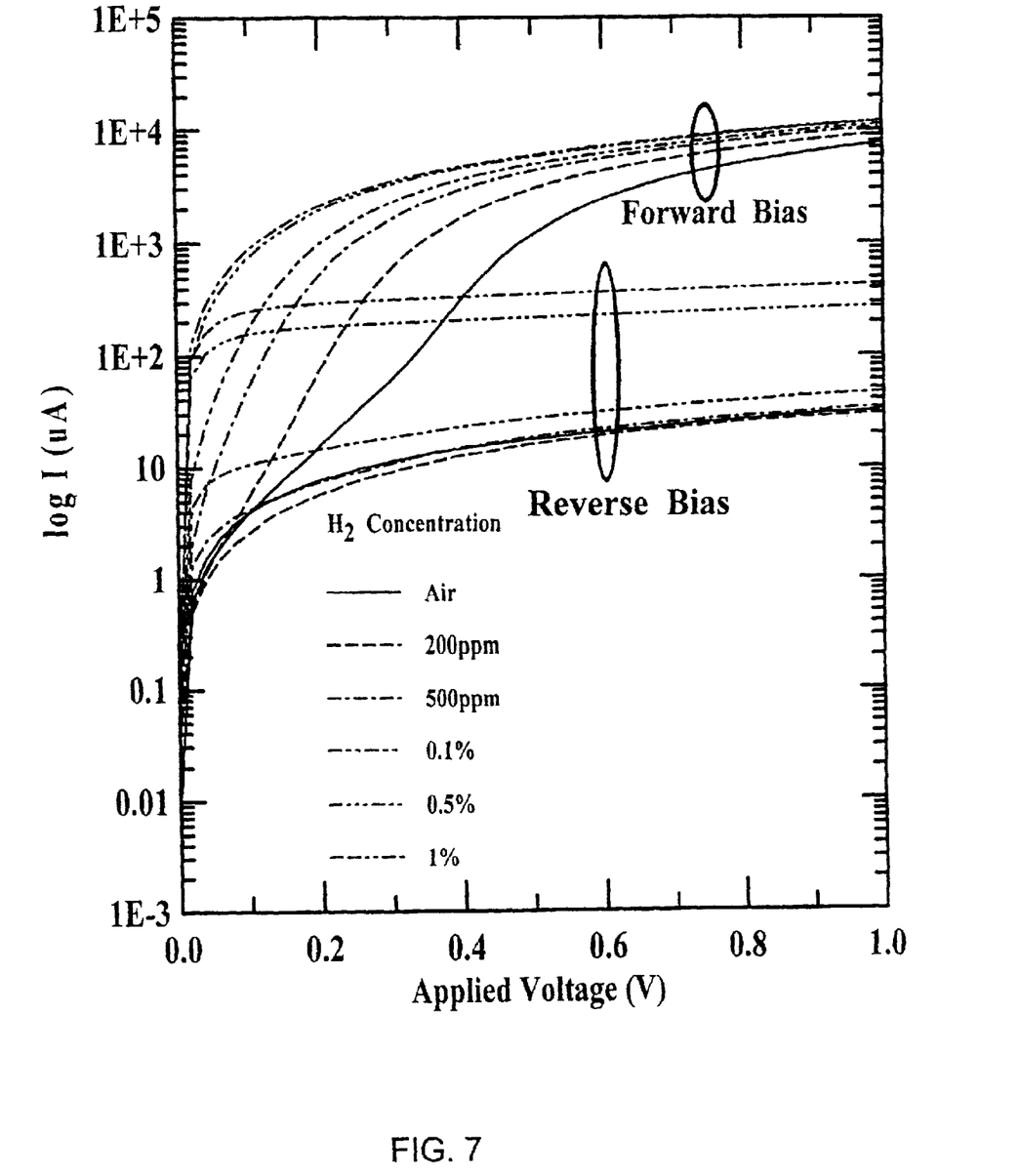
FIG. 7 shows the current-voltage characteristics of the hydrogen sensor prepared according to a second preferred embodiment of the present invention, when it was used to measure air and atmospheres which contain 200 ppm, 500 ppm, 1000 ppm, 5000 ppm and 10000 ppm of hydrogen, respectively.

FIG. 7 shows the current-voltage characteristics of the hydrogen sensor prepared in this example, when it was used to measure air and atmospheres which contain 200 ppm, 500 ppm, 1000 ppm, 5000 ppm and 10000 ppm of hydrogen, respectively. Due to the decrease of Schottky barrier height as the hydrogen content increases, correspondingly the current becomes larger. As it can be seen from FIG. 7, either a forward bias current or a reverse bias current increases as the hydrogen content increases. Moreover, it is obvious that the increase of a reverse current is proportional to the hydrogen content.

Figure 8:
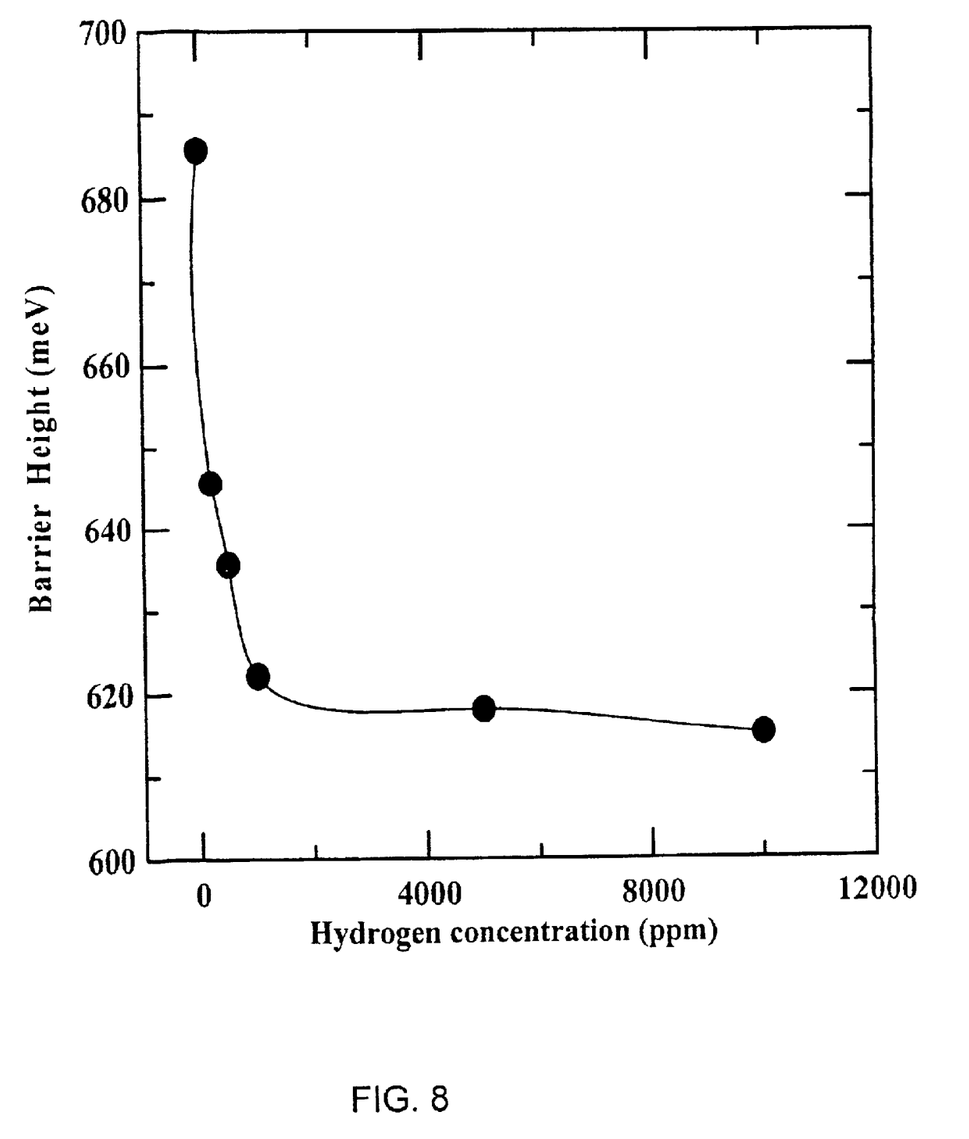
FIG. 8 shows the Schottky barrier height as a function of hydrogen content for the hydrogen sensor prepared according to the second preferred embodiment of the present invention.

FIG. 8 shows the Schottky barrier height as a function of hydrogen content for the hydrogen sensor prepared in this example. The barrier height in air is about 686 meV and it decreases along with an increase of the hydrogen content. When the hydrogen content is larger than 0.5%, the barrier height reaches a minimum and the forward current conduction is very close to the Ohmic contact.

Figure 9:
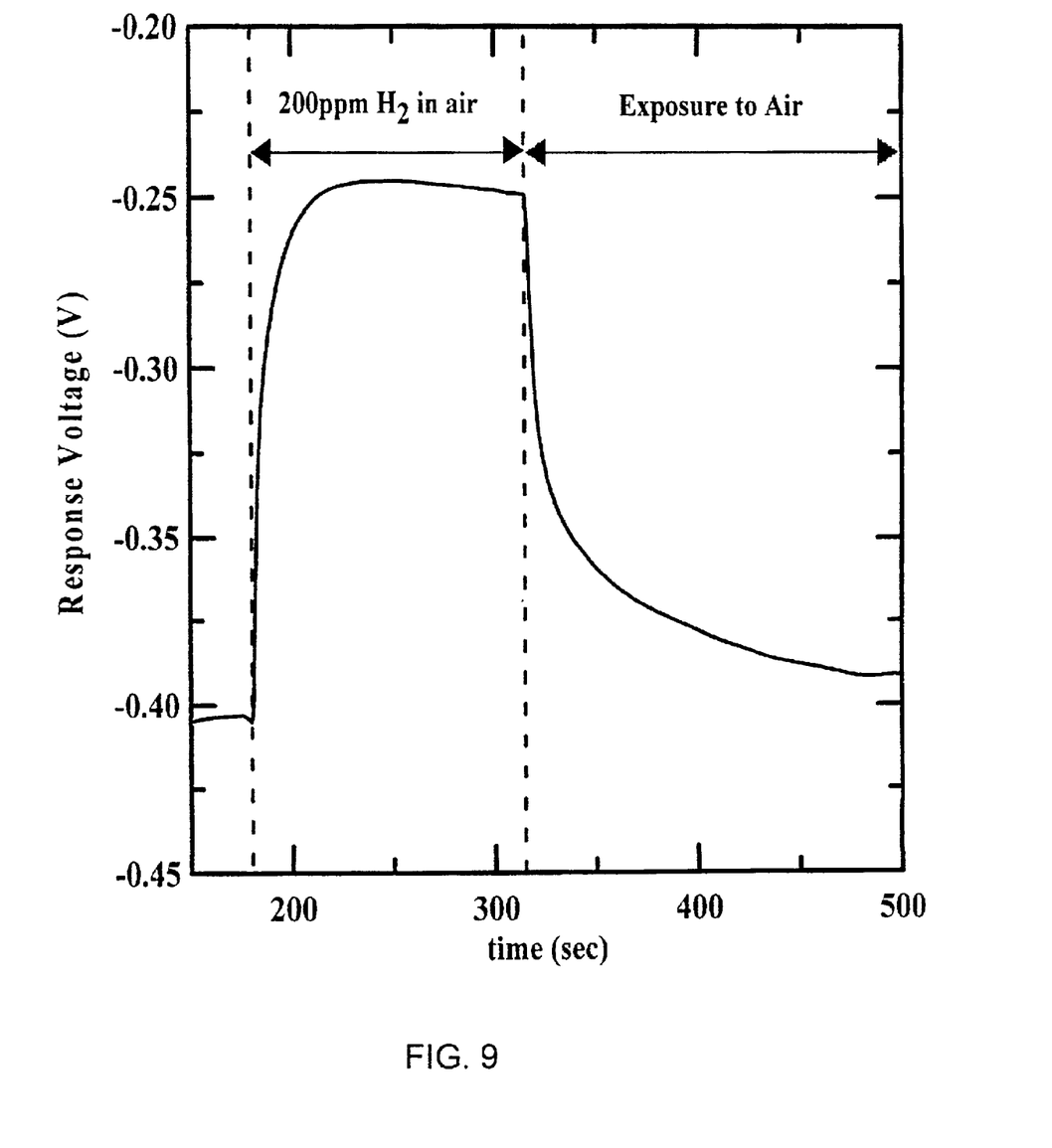
FIG. 9 shows transient responses measured at 125° C. for the hydrogen sensor prepared according to the second preferred embodiment of the present invention. An air flow containing 200 ppm of hydrogen was introduced into a test chamber at 500 ml/min. The reverse current of 7 mA was maintained between the two electrodes of the Schottky contact metal layer 18 and the Ohmic contact metal layer 16.

FIG. 9 shows transient responses measured at 125° C. for the hydrogen sensor prepared in this example. The air flow containing 200 ppm of hydrogen was introduced into the test chamber at a flow rate of 500 ml/min. The reverse current of 7 mA was maintained. Due to the dipole layer formed by the dissociated hydrogen atoms, the reverse current increases. Correspondingly, the voltage between the two electrodes decreases for about 0.15 V. On the other hand, when the hydrogen gas was turned off, the sensor was exposed to air. Therefore, the hydrogen atoms are desorbed from the surface of the Pd metal by recombining into hydrogen molecules or forming water molecules with oxygen. This results in recovering the voltage back to the origin. It can be seen from FIG. 9 that the reaction time of the sensor is about 5 seconds and the recovery time is about 20 seconds.

Figure 10:
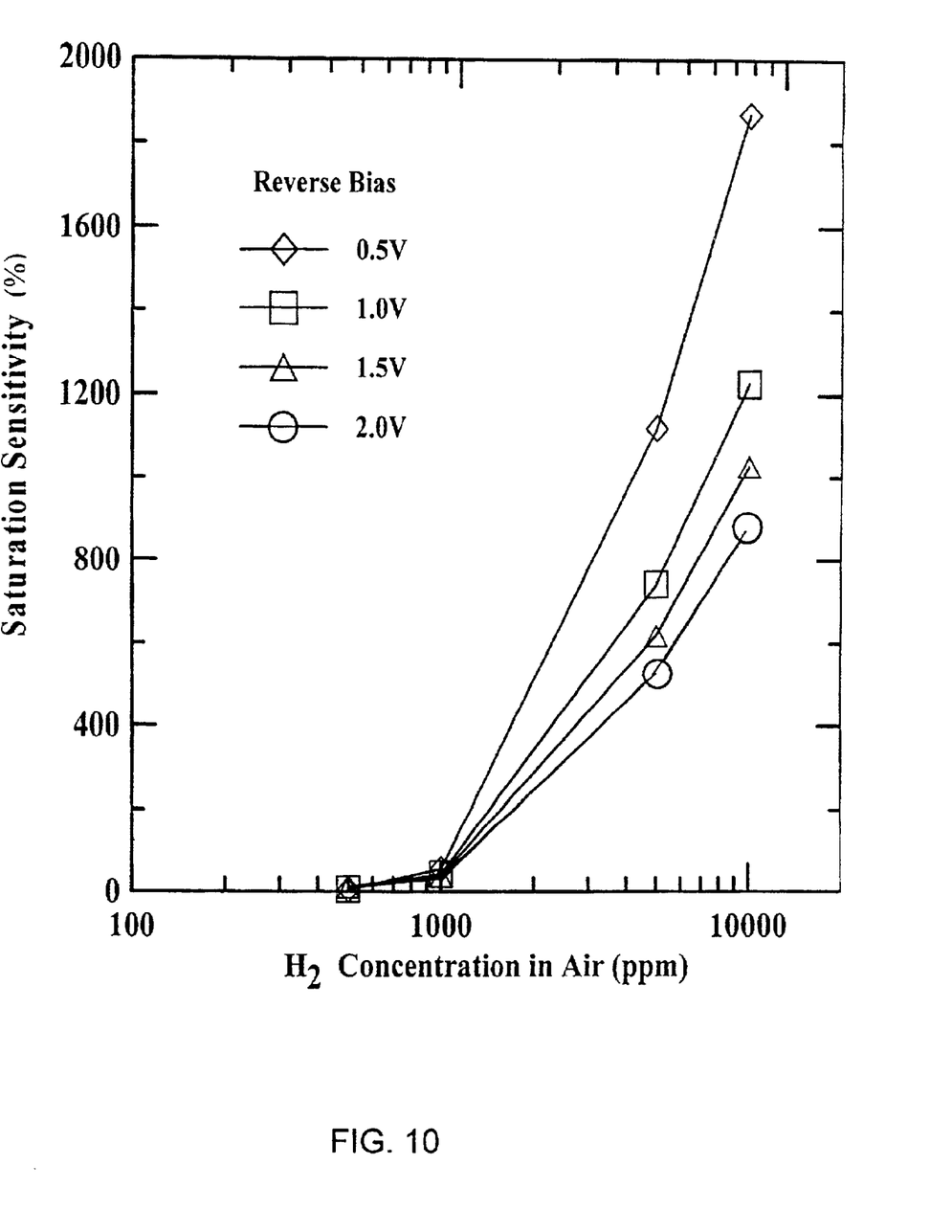
FIG. 10 shows the saturation sensitivity as a function of hydrogen content for the hydrogen sensor prepared according to the second preferred embodiment of the present invention under various reverse voltages of 0.5 V (blank diamond), 1.0 V (blank square), 1.5 V (blank triangle) and 2.0 V (blank circle), respectively.

FIG. 10 shows the saturation sensitivity as a function of hydrogen content for the hydrogen sensor prepared in this example. The results in FIG. 10 clearly show that the sensitivity (S) increases monotonically along with the increase of the hydrogen content. At a reverse bias of 0.5 V, a saturation sensitivity of the hydrogen sensor can reach up to 1835% in the air atmosphere containing 1% hydrogen. The saturation sensitivity can reach 4.3% even in the air atmosphere containing 200 ppm hydrogen (not shown in the drawing).

Figure 11:
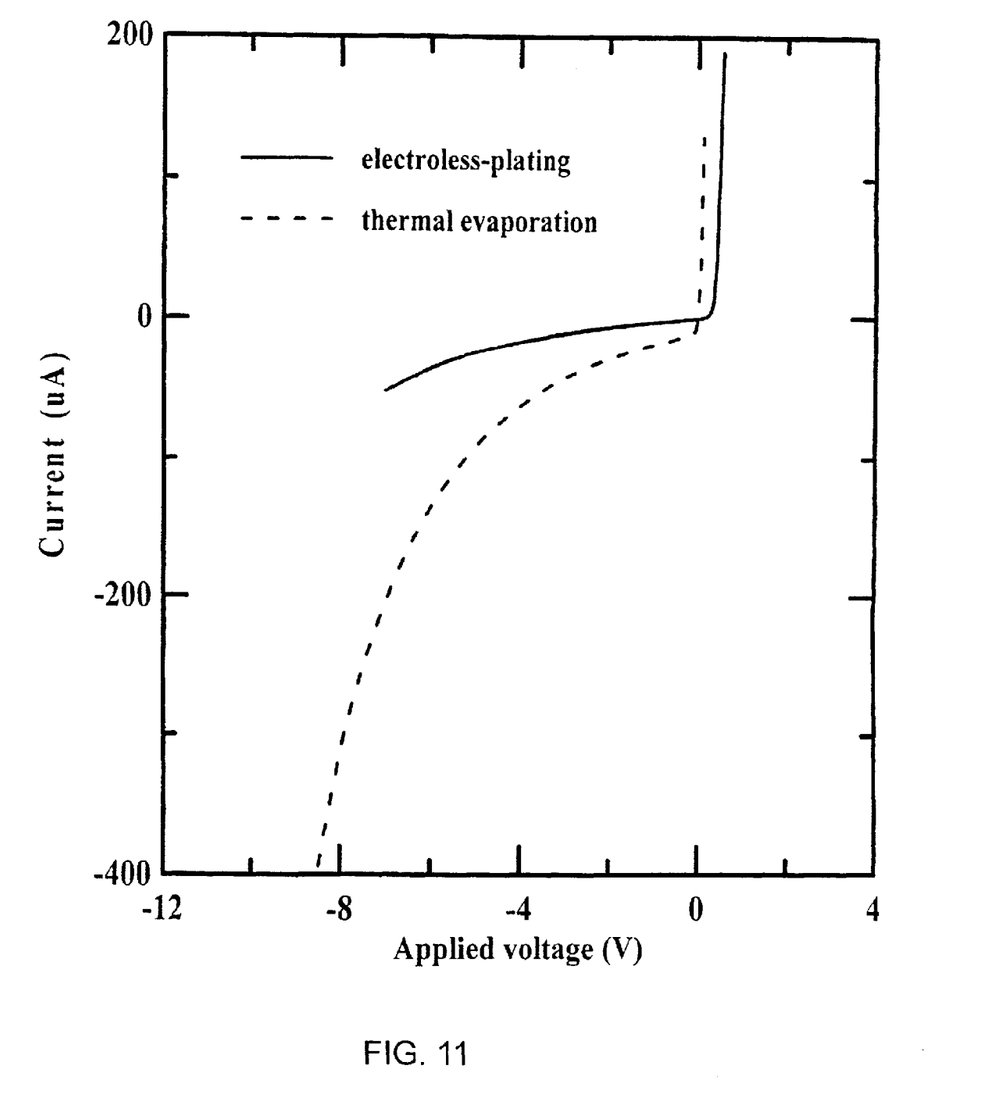
FIG. 11 shows the current-voltage characteristics of the hydrogen sensors prepared according to the first and second preferred embodiments of the present invention, wherein the Schottky contact metal layer 18 of the former was formed by vacuum evaporation (the dot line) and that of the latter was formed by electroless plating (the solid line).

FIG. 11 shows the current-voltage characteristics of the hydrogen sensors prepared according to Example 1 and Example 2, from which it can been seen that the latter (the solid line) has a better performance in term of the Schottky electric characteristic in comparison with the former (the dot line). This result is consistent with the theory of DIGS model proposed by Hasegawa, et al. [H. Hasegawa and H. Ohno, *J. Vac. Sci. Technol.*, B5, 1130 (1986)]. That is the surface of the semiconductor is vulnerable to the latent heat released from the condensation of metal vapor during vacuum evaporation, causing a surface state pinning of Fermi-level of semiconductor, and thus the Schottky barrier height is less susceptible to be affected. The electroless plating is a low-temperature fabrication process, which does not have this drawback.

Based on the above-mentioned disclosure, a hydrogen sensor according to the present invention not only has advantages of a small size, a simple fabrication process and a high feasibility of being integrated, but shows high linearity, high response time, high reproducibility and high sensitivity compared to a conventional hydrogen sensor.

Even though the present invention is disclosed through a preferred embodiment, the above-mentioned disclosure is not restrictive on the present invention. Any person skilled in the art can make various alterations and modifications without departure from the spirit and scope of the present invention. Therefore, the scope of the present invention is only limited by the claims appended hereinafter.

What is claimed:

1. A process for preparing a hydrogen sensor comprising the following steps:
    a) forming an n-type or p-type semiconductor film on a semiconductor substrate;
    b) forming a patterned first metal electrode on said semiconductor film, wherein said patterned first metal electrode forms an Ohmic contact with said semiconductor film; and
    c) forming a second metal electrode on said semiconductor film, said second metal electrode being isolated from said patterned first metal electrode, wherein said second metal electrode forms a Schottky contact with said semiconductor film, wherein a thickness of said second metal electrode and a material of which said second metal electrode is made enable a Schottky barrier height of said Schottky contact to decrease when hydrogen contacts said second metal electrode;
    wherein step b) comprises the following sub-steps:
        I. coating a photoresist layer on said semiconductor film;
        II. imagewise exposing said photoresist layer with a photomask;
        III. developing said imagewise exposed photoresist layer to transfer a pattern of said photomask to said photoresist layer, so that a patterned photoresist layer is formed, and thus said semiconductor film is partially exposed;
        IV. depositing a patterned first metal on the partially exposed semiconductor film; and
        V. lifting-off said patterned photoresist layer to form said patterned first metal electrode on said semiconductor film.

2. The process according to claim 1, further comprising thermal annealing said patterned first metal electrode after the formation of said patterned first metal electrode in step b), so that electric characteristics of said Ohmic contact are enhanced.

3. The process according to claim 2, wherein said thermal annealing is carried out at a temperature ranging from 300° C. to 500° C. for a period from 20 seconds to 5 minutes.

4. The process according to claim 1, wherein said depositing in sub-step IV) of step b) is carried out by physical vapor deposition.

5. The process according to claim 4, wherein said physical vapor deposition is vacuum evaporation.

6. A process for preparing a hydrogen sensor comprising the following steps:
    a) forming an n-type or p-type semiconductor film on a semiconductor substrate;
    b) forming a patterned first metal electrode on said semiconductor film, wherein said patterned first metal electrode forms an Ohmic contact with said semiconductor film; and
    c) forming a second metal electrode on said semiconductor film, said second metal electrode being isolated from said patterned first metal electrode, wherein said second metal electrode forms a Schottky contact with said semiconductor film, wherein a thickness of said second metal electrode and a material of which said second metal electrode is made enable a Schottky barrier height of said Schottky contact to decrease when hydrogen contacts said second metal electrode;

wherein step c) comprises the following sub-steps:
  i. coating a photoresist layer on a whole surface of said semiconductor film containing said patterned first metal electrode;
  ii. imagewise exposing said photoresist layer with a photomask;
  iii. developing said imagewise exposed photoresist layer to transfer to a pattern of said photomask to said photoresist layer, so that a patterned photoresist layer is formed, and thus said semidonductor film is partially exposed;
  iv. depositing a second metal on the partially exposed semiconductor film; and
  v. lifting-off said patterned photoresist layer to form said second metal electrode on said semiconductor film.

7. The process according to claim 6, wherein said depositing in sub-step iv) is carried out by physical vapor deposition.

8. The process according to claim 7, wherein said physical vapor deposition is vacuum evaporation.

9. The process according to claim 7, wherein said second metal is Pd, Pd alloy or Pt.

10. The process according to claim 9, wherein said second metal is Pd.

11. The process according to claim 6, said depositing in sub-step iv) is carried out by electroless plating.

12. The process according to claim 11, wherein said second metal is Pd, Pd alloy or Pt.

13. The process according to claim 12, wherein said second metal is Pd.

14. The process according to claim 13, wherein said electroless plating comprises contacting said partially exposed semiconductor film with a plating solution for a period of time, wherein said plating solution is an aqueous solution comprising palladium ions, a complexing agent, a reducing agent, a pH buffer and a stabilizer.

15. The process according to claim 14, wherein said palladium ions are provided by dissolving a palladium salt or palladium halide into water, said complexing agent is selected from the group consisting of ethylenediamine, tetramethylethylenediamine, ethylenediaminetetraacetic acid (EDTA) and N,N,N',N'-tetrakis(2-hydroxypropyl)-ethylenediamine; and said reducing agent is selected from the group consisting of hydrazine, hypophosphite, borohydride and formaldehyde.

16. The process according to claim 14, wherein said plating solution has a pH value ranging from 9 to 12.

17. The process according to claim 14, wherein said pH buffer is boric acid or ammonia solution.

18. The process according to claim 14, wherein said electroless plating, prior to contacting said partially exposed semiconductor film with said plating solution, further comprises undergoing a sensitization treatment by contacting said partially exposed semiconductor film with a sensitizing solution; and subsequently undergoing an activation treatment by contacting said partially exposed semiconductor film with an activating solution.

19. The process according to claim 18, wherein said sensitizing solution is an acidic solution containing stannous ions, and said sensitization treatment undergoes 5 to 10 minutes; wherein said activating solution is an acidic solution containing palladium ions, and said activation treatment undergoes 5 to 10 minutes.

20. The process according to claim 14, wherein said electroless plating comprises contacting said partially exposed semiconductor film with said plating solution at a temperature of 20–70° C. for a period of time ranging from 1 minute to 1 hour.

21. The process according to claim 12, wherein said electroless plating comprises contacting said partially exposed semiconductor film with a plating solution for a period of time, wherein said plating solution is an aqueous solution comprising metal ions of said second metal electrode, a complexing agent, a reducing agent, a pH buffer and a stabilizer.

22. A process for preparing a hydrogen sensor comprising the following steps:
  a) forming an n-type or p-type semiconductor film on a semiconductor substrate;
  b) forming a pattered first metal electrode on said semiconductor film, wherein said pattered first metal electrode forms an Ohmic contact with said semiconductor film; and
  c) forming a second metal electrode on said semiconductor film, said second metal electrode being isolated from said pattered first metal electrode, wherein said second metal electrode forms a Schottky contact with said semiconductor film, wherein a thickness of said second metal electrode and a material of which said second metal electrode is made enable a Schottky barrier height of said Schottky contact to decrease when hydrogen contacts said second metal electrode;
wherein said semiconductor substrate is made of a semi-insulating InP or GaAs material.

23. A process for preparing a hydrogen sensor comprising the following steps:
  a) forming an n-type or P-type semiconductor film on a semiconductor substrate;
  b) forming a patterned first metal electrode on said semiconductor film, wherein said patterned first metal electrode forms an Ohmic contact with said semiconductor film; and
  c) forming a second metal electrode on said semiconductor film, said second metal electrode being isolated from said pattered first metal electrode, wherein said second metal electrode forms a Schottky contact with said semiconductor film, wherein a thickness of said second metal electrode and a material of which said second metal electrode is made enable a Schottky barrier height of said Schottky contact to decrease when hydrogen contacts said second metal electrode;
wherein said semiconductor film formed in step a) is an n-type III-V compound.

24. The process according to claim 23, wherein said n-type III-V compound has a doping concentration of $5 \times 10^{15}$ to $1 \times 10^{18}$ cm$^{-3}$.

25. The process according to claim 23, wherein said n-type III-V compound has a thickness of 0.050 micron to 10 micron.

26. The process according to claim 23, wherein said n-type III-V compound is n-type InP (n-InP) or n-type GaAs.

27. The process according to claim 26, wherein said n-type III-V compound is n-InP.

28. A process for preparing a hydrogen sensor comprising the following steps:
  a) forming an n-type or p-type semiconductor film on a semiconductor substrate;
  b) forming a patterned first metal electrode on said semiconductor film, wherein said patterned first metal electrode forms an Ohmic contact with said semiconductor film; and c) forming a second metal electrode on said semiconductor film, said second metal electrode being isolated from said patterned first metal electrode, wherein said second metal electrode forms a Schottky contact with said semiconductor film, wherein a thickness of said second metal electrode and a material of which said second metal electrode is made enable a Schottky barrier height of said Schottky contact to decrease when hydrogen contacts said second metal electrode;

wherein said semiconductor film is formed by a metal organic chemical vapor deposition or molecular beam epitaxy deposition in step a).

29. A process for preparing a hydrogen sensor comprising the following steps:
   a) forming an n-type or p-type semiconductor film on a semiconductor substrate;
   b) forming a patterned first metal electrode on said semiconductor film, wherein said patterned first metal electrode forms an Ohmic contact with said semiconductor film; and
   c) forming a second metal electrode on said semiconductor film, said second metal electrode being isolated from said patterned first metal electrode, wherein said second metal electrode forms a Schottky contact with said semiconductor film, wherein a thickness of said second metal electrode and a material of which said second metal electrode is made enable a Schottky barrier height of said Schottky contact to decrease when hydrogen contacts said second metal electrode;

wherein said patterned first metal electrode is an AuGe alloy or AuGeNi alloy.

30. The process according to claim 29, wherein said patterned first metal electrode is an AuGe alloy.

31. A process for preparing a hydrogen sensor comprising the following steps:
   a) forming an n-type or p-type semiconductor film on a semiconductor substrate;
   b) forming a patterned first metal electrode on said semiconductor film, wherein said patterned first metal electrode forms an Ohmic contact with said semiconductor film; and
   c) forming a second metal electrode on said semiconductor film, said second metal electrode being isolated from said patterned first metal electrode, wherein said second metal electrode forms a Schottky contact with said semiconductor film, wherein a thickness of said second metal electrode and a material of which said second metal electrode is made enable a Schottky barrier height of said Schottky contact to decrease when hydrogen contacts said second metal electrode;

wherein said patterned first metal electrode has a thickness of 0.30 micron to 5 micron.

32. The process according to claim 31, wherein said patterned first metal electrode is an AuGe alloy.

33. A process for preparing a hydrogen sensor comprising the following steps:
   a) forming an n-type or p-type semiconductor film on a semiconductor substrate;
   b) forming a patterned first metal electrode on said semiconductor film, wherein said pattered first metal electrode forms an Ohmic contact with said semiconductor film; and
   c) forming a second metal electrode on said semiconductor film, said second metal electrode being isolated from said patterned first metal electrode, wherein said second metal electrode forms a Schottky contact with said semiconductor film, wherein a thickness of said second metal electrode and a material of which said second metal electrode is made enable a Schottky barrier height of said Schottky contact to decrease when hydrogen contacts said second metal electrode;

wherein said second metal electrode has a thickness of 0.30 micron to 5 micron.

34. The process according to claim 33, wherein said second metal electrode is Pd.

35. A process for preparing a hydrogen sensor comprising the following steps:
   a) forming an n-type or p-type semiconductor film on a semiconductor substrate;
   b) forming a patterned first metal electrode on said semiconductor film, wherein said pattered first metal electrode forms an Ohmic contact with said semiconductor film; and
   c) forming a second metal electrode on said semiconductor film, said second metal electrode being isolated from said pattered first metal electrode, wherein said second metal electrode forms a Schottky contact with said semiconductor film, wherein a thickness of said second metal electrode and a material of which said second metal electrode is made enable a Schottky barrier height of said Schottky contact to decrease when hydrogen contacts said second metal electrode;

wherein said second metal electrode has a C shape or a C-like shape, and said pattered first metal electrode has a shape corresponding to the shape of said second metal electrode such that said pattered first metal electrode is encompassed by said second metal electrode.

36. A process for preparing a hydrogen sensor comprising the following steps:
   a) forming an n-type or p-type semiconductor film on a semiconductor substrate;
   b) forming a patterned first metal electrode on said semiconductor film, wherein said pattered first metal electrode forms an Ohmic contact with said semiconductor film; and
   c) forming a second metal electrode on said semiconductor film, said second metal electrode being isolated from said patterned first metal electrode, wherein said second metal electrode forms a Schottky contact with said semiconductor film, wherein a thickness of said second metal electrode and a material of which said second metal electrode is made enable a Schottky barrier height of said Schottky contact to decrease when hydrogen contacts said second metal electrode;

wherein said pattered first metal electrode has a C shape or a C-like shape, and said second metal electrode has a shape corresponding to the shape of said patterned first metal electrode such that said second metal electrode is encompassed by said patterned first metal electrode.

* * * * *